United States Patent [19]

Chevalier et al.

[11] Patent Number: 5,194,036

[45] Date of Patent: Mar. 16, 1993

[54] METHOD FOR GRADING CARCASSES OF LARGE CATTLE, CALVES, HOGS, OR SHEEP AND DEVICE FOR IMPLEMENTATION THEREOF

[75] Inventors: Patrick Chevalier, Olle; Michele Villemin, Ormesson Sur Marne; Janusz Plusa, Sucy En Brie; Jean Leclere, Creteil, all of France

[73] Assignee: Normaclass, Paris, France

[21] Appl. No.: 834,836

[22] Filed: Feb. 13, 1992

[30] Foreign Application Priority Data

Feb. 14, 1991 [FR] France ............................ 91 02297

[51] Int. Cl.⁵ .......................... B07C 3/18; A22C 18/00
[52] U.S. Cl. .................................. 452/198; 452/157; 358/93; 705/3.3
[58] Field of Search ............... 452/198, 179, 178, 184, 452/180, 157, 163; 358/93, 107; 356/376, 445

[56] References Cited

U.S. PATENT DOCUMENTS

| | | | |
|---|---|---|---|
| 4,256,569 | 3/1981 | Wallace | 209/3.3 |
| 4,597,495 | 7/1986 | Knosby | 452/198 |
| 4,939,574 | 7/1990 | Petersen et al. | 358/93 |
| 4,962,568 | 10/1990 | Rudy et al. | 452/157 |

FOREIGN PATENT DOCUMENTS

| | | |
|---|---|---|
| 0046704 | 3/1982 | European Pat. Off. . |
| 0321981 | 6/1989 | European Pat. Off. . |
| 0361625 | 4/1990 | European Pat. Off. . |
| 3049589 | 7/1982 | Fed. Rep. of Germany . |
| 2462205 | 2/1981 | France . |
| 2545010 | 11/1984 | France . |
| 2608899 | 7/1988 | France . |
| 2000280 | 1/1979 | United Kingdom . |

*Primary Examiner*—Willis Little
*Attorney, Agent, or Firm*—Oliff & Berridge

[57] ABSTRACT

In a method and apparatus for grading carcasses, a carcass is rested on a support along a lengthwise face of the carcass as well as along a dorsal face, near the lower part thereof, namely near the part located toward the animal's neck. The support is pivoted for positioning the carcass angularly to take images from various angles at the hindquarters, thigh, upper part of the backbone, and front part of the carcass corresponding to the lower zone thereof. The recorded images are stored in the memory of a computer which already contains the weight and length measurements of the carcass. The support is retracted to remove the carcass from the surface on which it rests. The recorded image information is compared with stored theoretical data to grade the carcass. The support can be a belt forming a first resting surface with a movable flap forming the second surface or an element with two fixed surfaces. The support is moved vertically to optimize its support of the carcass.

18 Claims, 5 Drawing Sheets

METHOD FOR GRADING CARCASSES OF LARGE CATTLE, CALVES, HOGS, OR SHEEP AND DEVICE FOR IMPLEMENTATION THEREOF

BACKGROUND OF THE INVENTION

1. Field of the Invention

The invention relates to the grading of carcasses of animals such as large cattle, calves, hogs, or sheep.

2. Description of Related Developments

There are major differences in morphology and fat status of animals of a given species. Hence, after the animals have been slaughtered, the carcasses need to be graded to determine the price to be paid to the stock raiser and to determine the ultimate utilization, which is a function of the quality of each carcass.

This grading takes place at the end of the abattoir conveyors, namely after evisceration and preparation of the animals, on whole carcasses (calves, sheep) or half-carcasses (large cattle, hogs) suspended from a conveyor that advances continuously or stepwise.

In the case of large cattle, two independent criteria are used to grade the carcasses: conformation, and fat status. A European Community descriptive table based on visual assessment of these two criteria was officially published in the EC regulations of Apr. 28, 1981 and Oct. 12, 1981.

Conformation takes into account the quantity of meat on the carcass as a function of its dimensions. Conformation is determined by evaluating muscle shapes and thicknesses. Five grades have been defined, each characterized by one of the letters in the word EUROP. The conformation quality goes from grade E, which corresponds to a carcass of excellent conformation with convex profiles and excellent muscle development, down to grade P, which corresponds to a mediocre conformation with concave profiles and very meager muscle development.

Fat status is evaluated by examining the covering fat and the fat inside the rib cage. Five grades have been defined, each characterized by a number, from 1 for "very low" fat to 5 for "very high" fat.

Each conformation and fat status grade can be subdivided into three subgrades (+, =, −) to improve grading accuracy.

At the present time, the carcasses are graded by operators who inspect each carcass and assign to it a conformation grade or subgrade as well as a fat status grade or subgrade. It must however be borne in mind that this grading method, although it refers to an official table, is subjective in nature because it depends solely on visual assessment by an operator subject to varying work conditions. This brings about differences in the grading of a given carcass by different operators and in different abattoirs.

To overcome these disadvantages, the idea has been conceived of using devices that would provide a grading according to the EUROP European Community table that is less subjective and in particular more uniform over time and for different slaughter sites.

For this purpose, mechanical measuring methods have been devised. One solution, described in the Auge French patents No. 79 19310 and No. 80 17947, which is limited to evaluating the conformation grade, is unsatisfactory because each carcass to be graded has to be immobilized, made to contact a number of measuring elements, such as feelers, the measurements must be read, and finally the measuring elements must be removed, which may be troublesome at high speeds.

Devices also exist that measure fat status using a probe which must be driven into the tissues at particular points on the carcass and which give a measurement of the thickness of fat and muscle traversed by the probe. One such device is marketed under the tradename Fat-0-Meter and is made by SKF, Hennessy. Manual implementation is expensive and incompatible with high speeds. Automation is difficult because all carcasses are not the same size and are advancing along the conveyor.

Grading devices using video image analysis exist (Pfister SKG; Petersen, Danish patent application Ser. No. 6764/87), which yield a conformation grading by analyzing the contour of certain parts of the carcass and a fat grading by analyzing the contrast observed between fat and muscle. This device, studied on hogs, can provide an estimate of the meat yield but does not give satisfactory results for measuring the actual yield. In large cattle, whose carcasses are more complex than those of hogs, the device which is in the form of an enclosure containing a single video camera, does not produce grading according to the EUROP table sufficiently accurately and requires a manual probe to supplement the video measurements.

SUMMARY OF THE INVENTION

An object of the invention is to provide a method and a device that enables animal carcasses to be graded automatically by means that do not come into physical contact with the carcasses, which means can be installed along the conveyor, after weighing, which supplies information from an analysis of a half-carcass or whole carcass, whatever the size, weight, shape, and breed of the carcass in question, and which can grade about a hundred carcasses per hour for conformation and fat status. This invention has applicability to the grading of full carcasses or parts thereof, such as half carcasses, and such a full or partial carcass will be referred to in the following specification and claims as a "carcass".

For this purpose, this process comprises resting a carcass on its lengthwise face corresponding to the axis of symmetry of the carcass, as well as on its dorsal face, near the lower part thereof, namely near the part located toward the animal's neck on a positioning element; positioning the carcass by moving the positioning element angularly and recording images of the carcass from various angles at the hindquarters, thigh, upper part of the backbone, and front part of the carcass corresponding to the lower zone thereof; storing these images in the memory of a computer which already contains the weight and length measurements of the carcass; removing the latter from the surfaces on which it rests, then processing the recorded information, using theoretical data to grade the carcass.

The theoretical information results from the synthesis of data previously collected in a large volume and processed statistically relative to the EUROP reference grade, which allows the grading of each carcass to be determined in a uniform fashion relative to the EUROP table.

Another characteristic of this process comprises taking at least one image of the inner face of the carcass, sending this information to the computer, and processing this information, taking into account a large volume of data previously collected and processed statistically relative to grading of fat status according to the European Community table. This processing allows the fat status grade to be determined with complete fidelity according to the European Community table.

Advantageously, this method comprises first weighing each carcass to be graded, whereby the measured weight gives information on the length of the carcass, which is used to make a first heightwise position adjustment of the support of the carcass, then making an optical measurement of its length, which supplies information used to set precisely the heightwise position of the support of the carcass.

According to a first embodiment of this method, the carcass is lighted directly on the camera side, with a contrast being produced between the carcass and its background.

According to another embodiment of this method, the carcass is lighted indirectly by means of a luminous background that provides diffuse lighting of the entire carcass.

The goal in both cases is to achieve perfect definition of the contours of the carcass against its background.

A device for implementing this process comprises a positioning element for the carcass, which is in the form of a dihedron defined by two surfaces separated from each other by a substantially vertical edge, one of the faces of the dihedron being designed to rest against, for example, the cut face of the carcass and the other face of the dihedron being intended to rest against the dorsal face of the carcass near the lower part of the latter, the dihedron being mounted to pivot around a vertical axis and being retractable so that, when a carcass arrives, it is able to contact the dihedron; then, after imaging, the carcass can leave the dihedron to continue on its path along the conveyor.

According to one embodiment of the invention, the dihedron comprises two surfaces fixed relative to each other. The dihedron pivots about a vertical axis and moves translationally transverse to the direction of the conveyor.

In practice, the dihedron is placed in the plane of movement of the carcasses on the conveyor, serves to position a carcass, pivots this carcass so that it successively assumes several angular positions corresponding to the various imaging angles, returns the carcass to its original position, and is then retracted to release the carcass to allow it to continue along the conveyor.

According to another embodiment of this invention, the dihedron is comprised of an endless belt equipped with a washing system. The belt is mounted on vertical axes, with one face of the belt disposed essentially in the plane of the suspension hooks of the conveyor. The belt is driven at a speed corresponding to that of the conveyor and synchronously therewith. The belt support is mounted to pivot around a vertical axis and also has, at the downstream end of the belt, a flap disposed in a vertical plane, mounted to pivot between a position in which it is perpendicular to the run of the active face of the belt, and a position in which it is essentially in line therewith.

In this embodiment, the carcass first rests on the belt and is smoothly entrained in contact with the belt, which travels the same speed as that of the conveyor. Thereafter the belt can be slowed down at the same time as the conveyor so that the carcass can rest lightly against the flap which forms a stop, thereby preventing any undesired oscillating movements of the carcass. The dihedron comprising the belt and the flap pivots about its vertical axis so that the various images can be taken. When the dihedron returns to its original position, the flap is drawn into its retracted position, allowing the carcass to be released smoothly.

According to another characteristic of the invention, the width of the belt, namely its dimension considered in the heightwise direction, is substantially less than the length of the carcass, and the belt support is mounted so as to be vertically displaceable. The vertical support means of the belt and flap associated therewith are constituted by a slide on which the support of the belt and of the flap is mounted in articulated fashion, this slide itself being mounted on vertical columns, with vertical entrainment by means of a ballscrew.

According to another characteristic of the invention, the dihedron constituted by the belt and the flap is disposed in front of a light panel the height of which corresponds essentially to the distance between the ground and the conveyor carrying the carcasses. This lighted background provides indirect lighting of the carcass for cameras located on the side of the conveyor opposite to the light panel.

According to another characteristic of the invention, the vertical displacement movement of the dihedron designed to support a carcass is controlled, on one hand, by a weighing device for coarse setting and, on the other hand, by an optical device for measuring the carcass length, located upstream of the dihedron, for fine setting, so that the dihedron rests on the part of the animal's back located above its neck. The purpose is to effect a support on a rigid part and on a plane surface. Hence, this support must be effected above the neck.

According to another characteristic of the invention, the angle of rotation of the dihedron is on the order of 70° relative to the original position, and the images are taken by at least three cameras, with the optical axis of the first camera being perpendicular to the direction of the conveyor and with the other two cameras, having optical axes which lie in a horizontal plane, forming an angle of 45° and being disposed symmetrically relative to the first camera. Advantageously, the dihedron support is equipped with a camera designed to image the internal part of the carcass, said camera being associated with an additional lighting device and controlled by the device that measures the carcass length.

In any event, the invention will be properly understood with the aid of the description hereinbelow which refers to the attached schematic drawing representing one embodiment of the invention.

DESCRIPTION OF PREFERRED EMBODIMENTS

Figure 1:
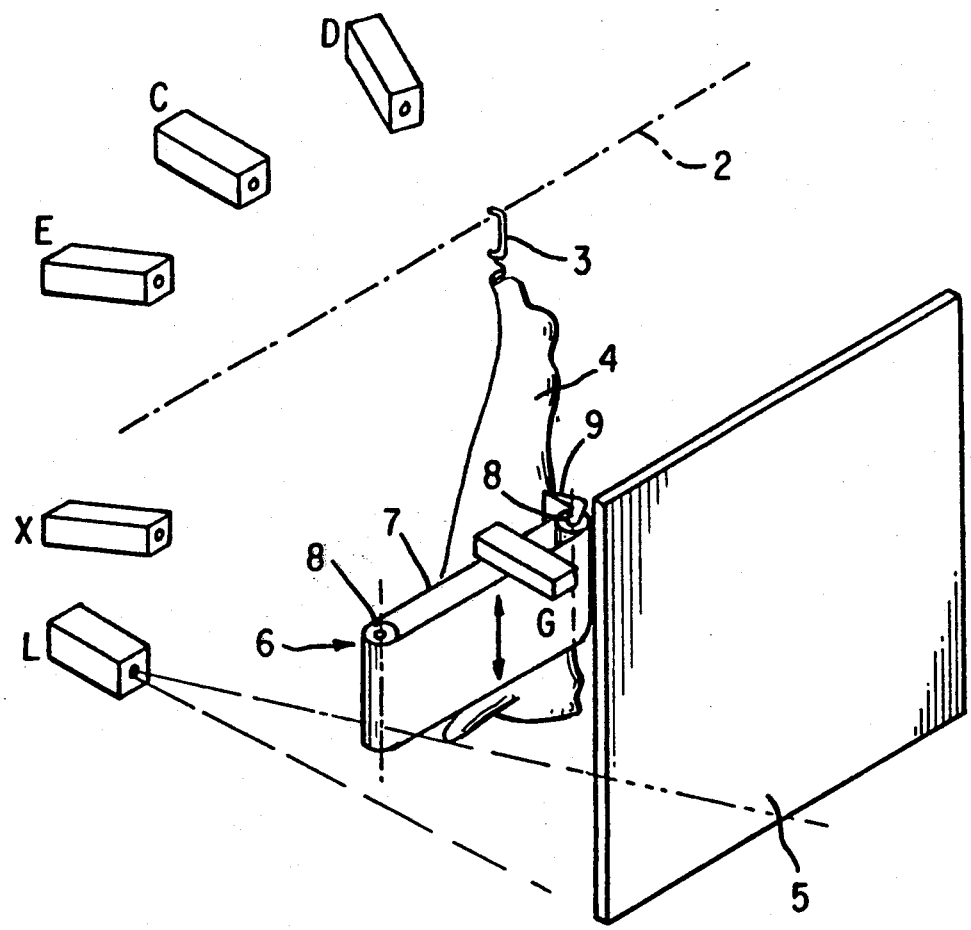
FIG. 1 is a schematic view of the layout of the various component parts of a carcass grading apparatus.
Figure 2:
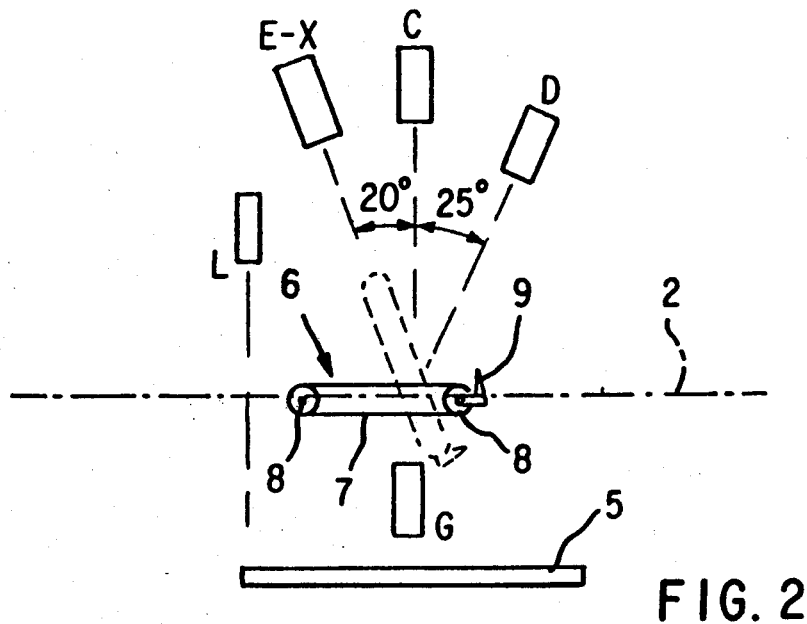
FIG. 2 is a top view of the apparatus shown in FIG. 1.

FIG. 1 shows a conveyor designated by reference numeral 2 to which are attached hooks 3, one of which is shown in the drawing, each for suspension of one carcass 4. The conveyor is not described in detail since it is of a known type which advances stepwise, for example.

On the side of the carcass corresponding to a cut face thereof is a light-diffusing element or screen 5, such as a box containing light sources having a ground glass face disposed toward the conveyor. The height of this screen is substantial and corresponds essentially to the height of the carcasses that are to be graded.

On the opposite side of conveyor 2, a number of cameras are mounted on fixed supports. A first camera L located upstream of screen 5 is designed to measure the length of the carcass. A camera C is disposed opposite screen 5. The optical axis of camera C is perpendicular to the direction of movement of the conveyor. Two other cameras D and E are preferably disposed such that the optical axes are contained in a horizontal plane including the optical axis of camera C and form an angle of 45° and form respective and approximately symmetrical angles of 25° and 20° relative to the optical axis of camera C. Cameras C, D, and E are designed to take images of the hindquarters, thigh, and top of the backbone of the carcass. A camera X located in the same vertical plane as camera E is designed to take an image of the lower part of the carcass corresponding to the front thereof.

Near screen 5, and between the latter and conveyor 2, is disposed a system for positioning each carcass. This system, designated by reference numeral 6, comprises an endless belt 7 mounted on two rollers 8 with vertical axes, as well as a flap 9 pivotable relative to belt 7 between a position in which it is perpendicular to the belt and a position in which it is substantially aligned therewith. The system also comprises a camera G designed to image the size and/or fat status of the, for example, interior of a split carcass near the sirloin, the camera G being equipped with additional spotlights and a washing system.

It is also possible to provide cameras (not shown in the drawing) with optical axes parallel to those of cameras C, D, or E operating with additional lighting designed to analyze the fat cover of the outer face of the carcass. Such cameras, as well as camera G, can provide image signals, the brightness of which corresponds to the amount of fat on the carcass.

Figure 3:
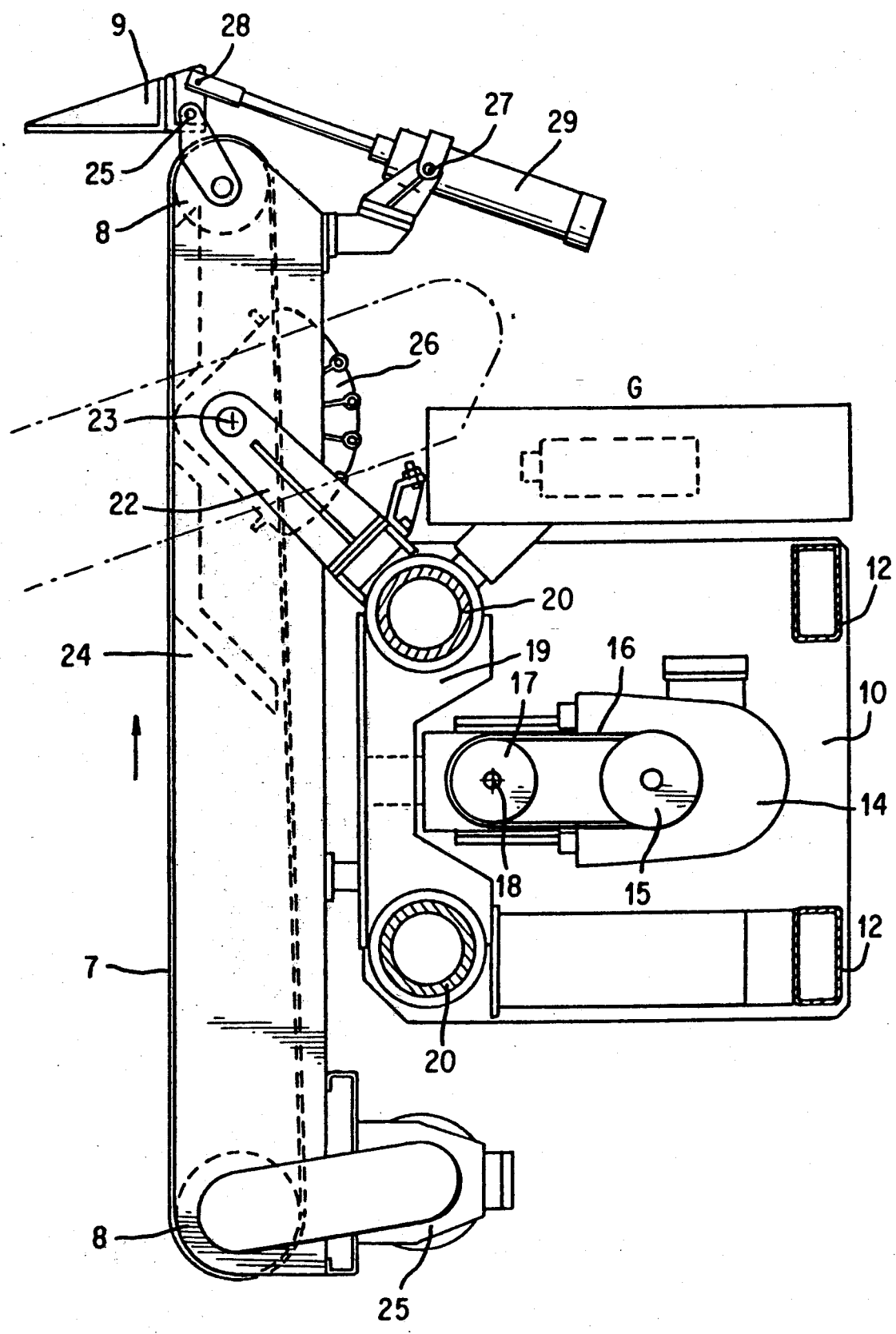
FIGS. 3 is a view from above partially in horizontal section of apparatus for positioning a carcass while the shapes are being recorded.
Figure 4:
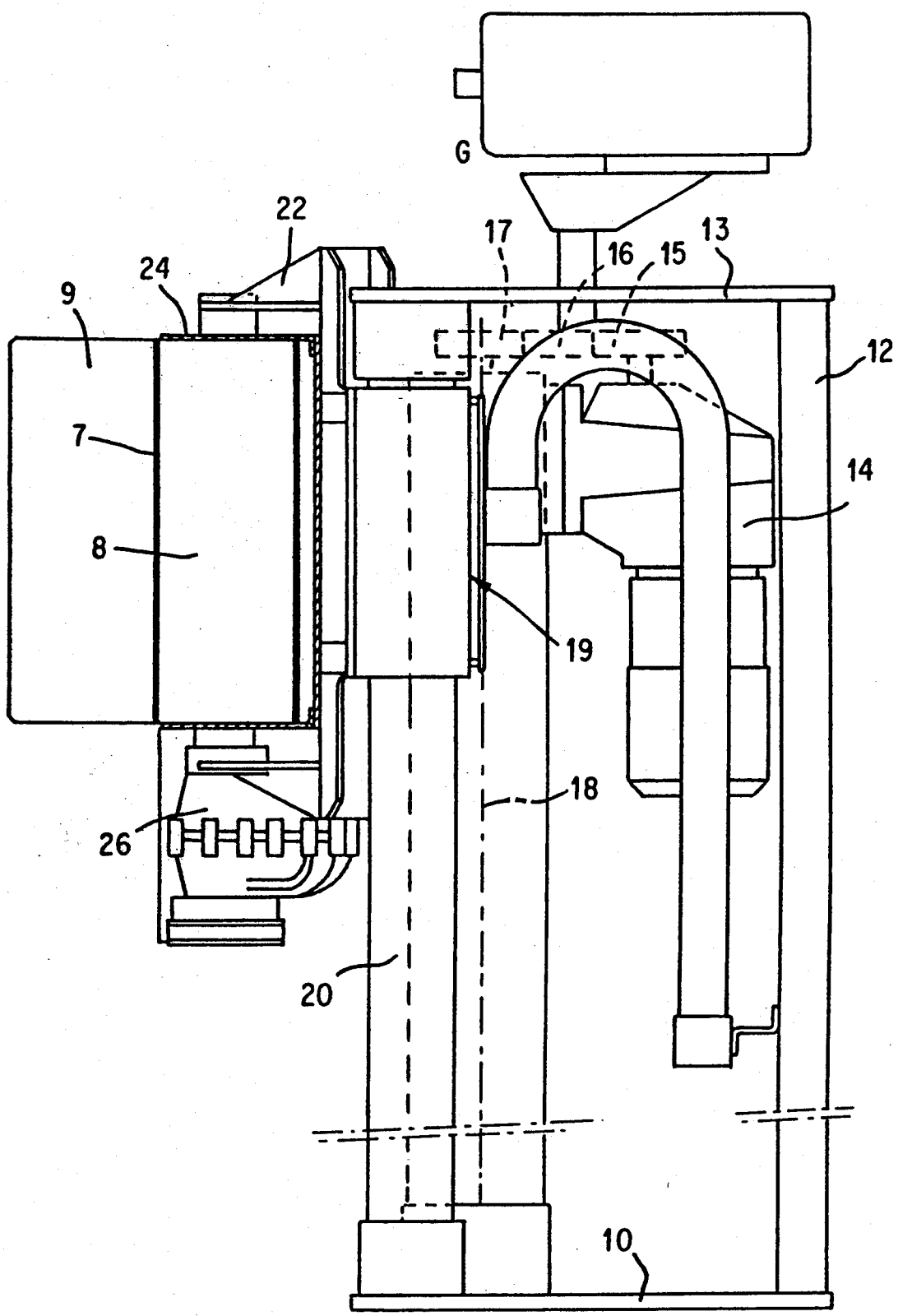
FIG. 4 is a side elevation of the holding and positioning apparatus shown in FIG. 3.

FIGS. 3 and 4 show in greater detail the positioning device of each carcass to be analyzed.

This device has a frame comprising a lower plate 10, vertical elements 12 and an upper plate 13. A motor 14 is mounted on the frame. The output shaft of motor 15 is equipped with a pulley 15 which, via a belt 16, drives a feed pulley 17 acting on a ballscrew having axis 18 shown in the drawing. This ballscrew drives a slide 19 mounted for vertical displacement on two columns 20 that are mounted on and extend between lower plate 10 and upper plate 13.

An arm 22 is attached to slide 19, at the free end of which arm a housing 24 is mounted to pivot around a vertical axis 23. The housing 24 has bearings for the two rollers 8 which guide belt 7. One of the rollers 8 is driven by a motor 25 synchronized with the movement of conveyor 2.

The housing 24 is rotated about axis 23 by a rotary screw 26. Housing 24 also has a vertical flap 9 mounted to pivot around the axis of pivot 25 between a position as shown in FIG. 3, wherein it is perpendicular to the belt and a position wherein it is positioned essentially parallel to belt 7. This pivoting movement of the flap 9 is achieved by a jack 29, the body of which is mounted to articulate around a vertical axis 27 on housing 24. The free end of jack 29 is articulated on a vertical axis 28 to flap 9.

This device operates as follows.

A weighing device (not shown) of a known type associated with the conveyor supplies a computer (not shown) with information on the weight of each carcass to be graded. Taking into account the relationship between weight and length of the carcass, the computer commands an approximate positioning of the assembly comprised of belt 7, flap 9, and camera G by controlling motor 14 to move slide 19. Camera L allows the exact length of each carcass analyzed to be determined. As a function of this length, the movable assembly composed of belt 7, flap 9, and camera G is precisely positioned heightwise in the same manner.

Since belt 7 is driven at the same speed as conveyor 2, the carcass comes in contact with the belt until it rests against flap 9. At this time, with the conveyor and the belt stopped, the pivoting assembly, comprised of belt 7 and flap 9, rotates about axis 23 through an angle of about 70°. Cameras E, D, and, optionally X take images of the carcass, after which the pivoting assembly returns to its original position, at which time images are taken with cameras C and G. When the imaging is over, flap 9 is tilted into its retracted position, thus releasing the carcass, which is carried away by conveyor 2. The information resulting from the images, to which is added the information on the length and weight of the carcass, is processed in the computer to determine the conformation of the carcass and its fat status.

As previously mentioned the analysis of the image information to determine grading and fat status is carried out by a computer. A general purpose microcomputer having a central processing unit (CPU), a ROM and a RAM can be utilized for this purpose. The theoretical statistical information regarding EUROP standards and data processing routines can be stored in the ROM. The images recorded by cameras C, D, E, L, X and G and the output from the weighing unit can be stored in the RAM. The CPU analyses the image data stored in the RAM against the grading data stored in the ROM to make grading determinations, which are then outputted to a soft copy and/or hard copy output device. The CPU can also be used to control drivers that acturate motor 14, motor 25, screw 26 and jack 29 at appropriate times.

It emerges from the foregoing that the invention contributes a great improvement to existing technology by furnishing a method and a device allowing animal carcasses to be faithfully graded in terms of conformation and fat status according to the EUROP table at a high speed on the conveyor itself.

Figure 5:
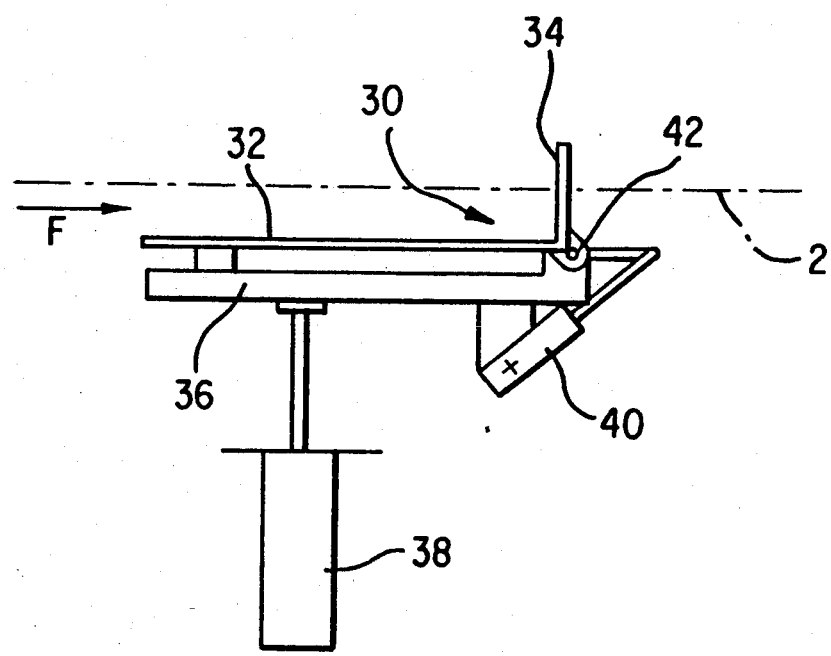
FIG. 5 is a top view of another embodiment of apparatus for positioning a carcass.
Figure 6:
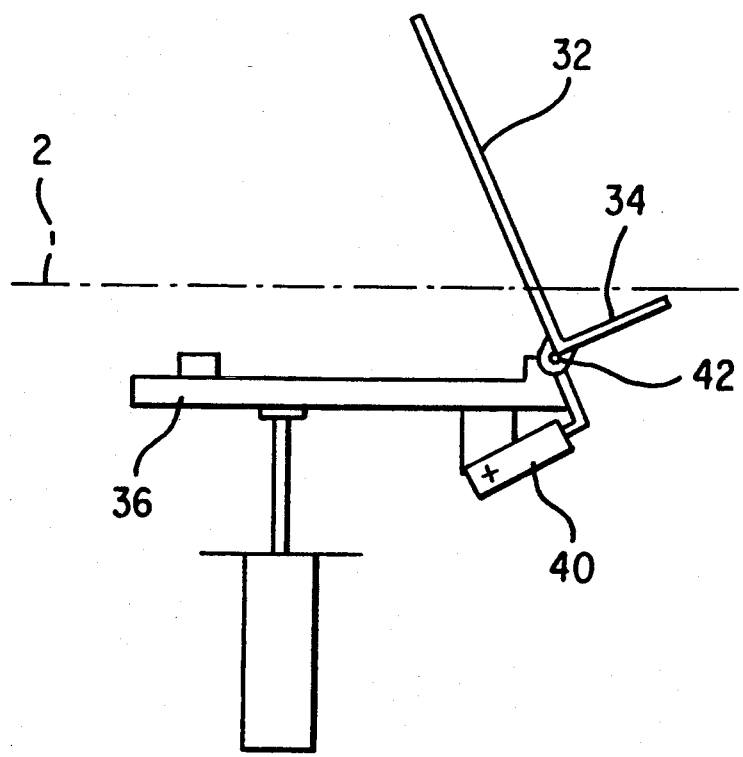
FIG. 6 shows the apparatus of FIG. 5 positioned for recording images of a carcass.
Figure 7:
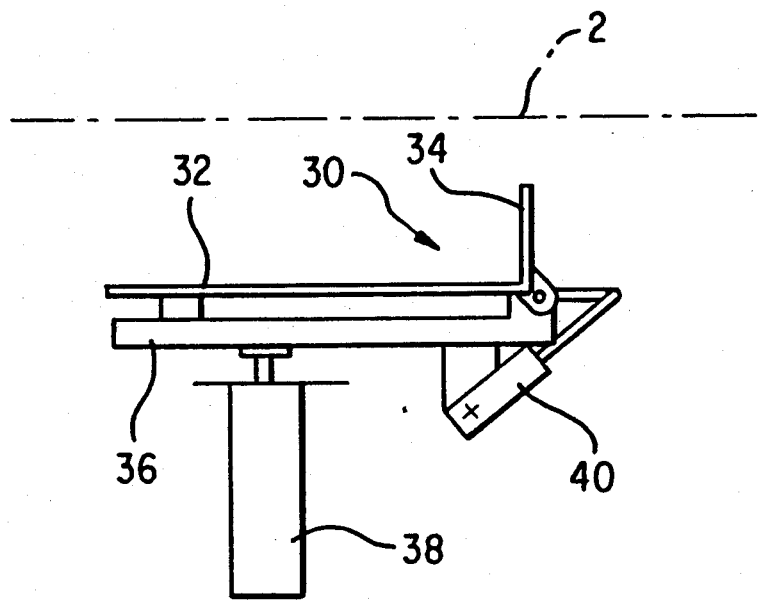
FIG. 7 shows the apparatus of FIG. 5 in retracted position.
Figure 8:
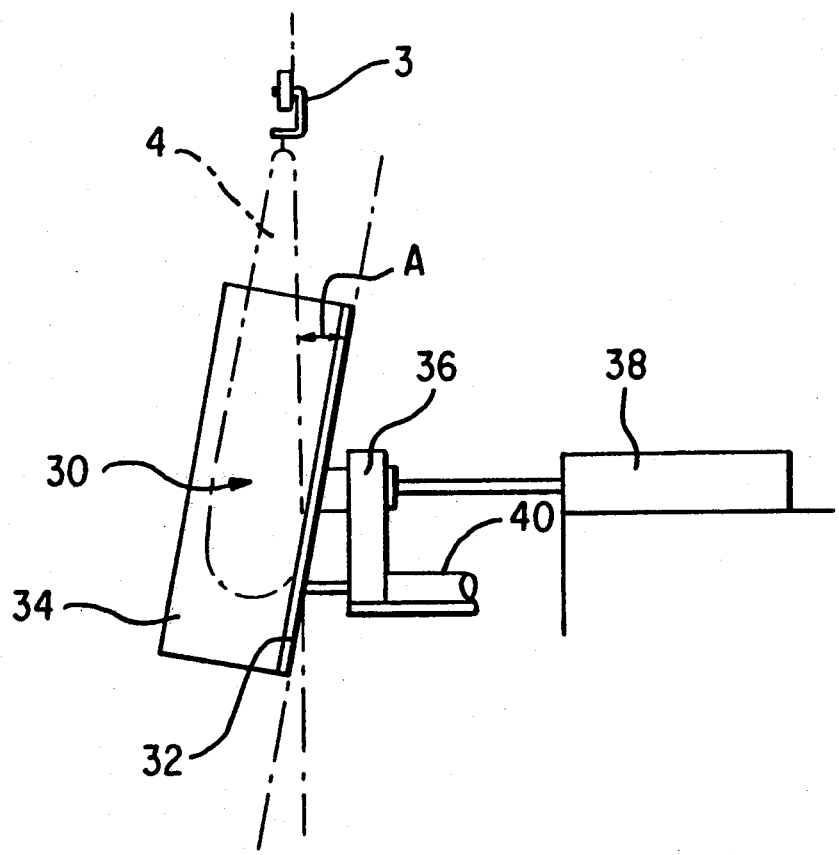
FIG. 8 is a side elevation of the apparatus shown in FIG. 5.

It goes without saying that the invention is not confined to the embodiment of this device described above as an example, but on the contrary covers all alternative embodiments. Thus, for example, the carcass-positioning system could be different and comprised, for example, a dihedron defined by two surfaces fixed relative to each other. This second embodiment is shown in FIGS. 5-8. FIG. 5 shows the dihedron 30 formed of a first surface 32, normally disposed parallel to the direction F of conveyor 2. The dihedron 30 includes a second surface 34 disposed preferably perpendicularly at the downstream edge of surface 32. The dihedron 30 is pivotally mounted on a frame 36 along an axis of pivot 42. The frame 36 is advanced to a position to receive a carcass, as shown in FIG. 5, and retracted from the carcass receiving position, as shown in FIG. 7, by a jack 38. The jack 38 and frame 36 may be fixed or may be mounted on the movable slide 19 shown in FIGS. 3 and 4 for vertical positioning with respect to a carcass on the conveyor 2. Once a carcass is received on dihedron 30 with a longitudinal surface resting on surface 32 and a dorsal surface resting on surface 34, the jack 40, which is mounted on frame 36, is retracted to pivot dihedron 30 about the axis of pivot 42, as shown in FIG. 6. In this position, the carcass is imaged by cameras C, D, E and X, as previously described. Subsequently the jacks 40 and 38 are operated to pivot the dihedron 30 to its original position and retract it from conveyor 2, respectively, as shown in FIG. 7, to allow the carcass to be carried away by the conveyor.

The contrasting of the carcass with its background could be achieved not by indirect lighting using ground glass but by direct lighting, with lights near the cameras, so that the carcass stands out against a contrasting background.

The device can be designed to handle one carcass or both carcasses obtained from the same carcass.

For simultaneous determination of the conformation and fat status, it is possible to use either different cameras or cameras associated with two different lighting modes. It is also possible to arrange the dihedron such that the surface 32 parallel to the direction of the conveyor is not vertical but inclined at an angle A (FIG. 8) of between 0° and 20° with respect to vertical, 7° for example. This surface is inclined downward and inward such that its edges are disposed one on either side of the vertical plane containing the conveyor. This ensures that the carcass will rest perfectly in the dihedron and will be securely immobilized. In view of this inclination, it is possible to provide, upstream of the dihedron, a slide (not shown) that gradually brings the carcass into the inclined position of the dihedron as the conveyor advances.

What is claimed is:

1. A method for grading livestock carcasses comprising the steps of: resting a carcass on a lengthwise face thereof and on a dorsal face thereof, near the lower part located toward a neck of the carcass, on positioning surfaces; moving the positioning surfaces to position the carcass angularly to record images of the carcass from several angles of portions of the carcass; recording image information from the carcass; storing the image information in the memory of a computer; storing information relating to the weight and length measurements of the carcass in the computer; removing the carcass from the positioning surfaces on which the carcass rests; and processing the recorded information in the computer to grade the carcass.

2. A method according to claim further comprising the steps of:
    recording at least one image of an inner face of the carcass, storing the inner face image information to the computer, and processing the inner face image information according to data stored in the computer to determine fat status of the carcass.

3. A method according to claim further comprising the steps of:
    weighing each carcass to be graded, whereby the measured weight gives information on the length of the carcass, and making a first heightwise position adjustment of the positioning surfaces of the carcass in accordance with the weight of the carcass.

4. A method according to claim 3, further comprising the steps of:
    after the weighing of each carcass, making an optical measurement of the length of the carcass, and precisely setting the heightwise position of the positioning surfaces of the carcass in accordance with said optical measurement.

5. A method according to claim wherein the step of recording image information of the carcass comprises lighting the carcass directly on a side from which the image information is taken, to produce a contrast between the carcass and a background.

6. A method according to claim wherein the step of recording image information of the carcass comprises lighting the carcass indirectly by a luminous background that provides diffuse lighting of the carcass.

7. Apparatus for grading livestock carcasses comprising: a positioning element for receiving a carcass mounted on a conveyor, said positioning element being in the form of a dihedron defined by two surfaces disposed angularly with respect to each other, one of the surfaces of the dihedron being adapted to rest against a lengthwise face of the carcass and the other surface of the dihedron being adapted to rest against a dorsal face of the carcass; a pivot for mounting the positioning element to pivot about a vertical axis; and means for retracting at least a portion of the positioning element whereby, a carcass carried by the conveyor is able to contact the dihedron to be positioned thereby and thereafter the carcass can leave the dihedron to continue on a path along the conveyor.

8. Apparatus as in claim 7, wherein the dihedron comprises two surfaces fixed relative to each other and further comprising means for imparting translational movement to the dihedron transversely to the direction of the conveyor.

9. Apparatus as in claim 7, wherein the dihedron comprises: an endless belt mounted on vertical axes, the belt having a face disposed essentially in the plane of suspension hooks of the conveyor; means for mounting the belt to pivot around a vertical axis; a flap disposed in a vertical plane at a downstream end of the belt; and means for mounting the flap to pivot between a position in which the flap is transverse to the said face of the belt, and a position in which the flap is retracted.

10. Apparatus as in claim 9, wherein the belt is positioned with the width thereof being substantially vertically oriented, said belt width being less than the length of a carcass, and further comprising a belt support means for mounting the belt for vertical displacement.

11. Apparatus as in claim 10, wherein the belt support means comprises a slide on which the belt and the flap are mounted; at least one vertical column for supporting the slide for vertical movement; and means for moving the slide vertically on said at least one column.

12. Apparatus as in claim 9, wherein said belt comprises drive means for driving the belt synchronously with the conveyor.

13. Apparatus as in claim 9, further comprising a light panel, said dihedron being disposed in front of the light panel.

14. Apparatus as in claim 7, further comprising a weighing device for weighing each carcass; means responsive to the weighing device for effecting a coarse setting of the vertical position of the dihedron; and an optical device located upstream of the dihedron for measuring the length of a carcass, and means responsive to said optical device for effecting a fine setting of the vertical position of the dihedron, so that the dihedron rests on a part of the carcass located above the neck of the carcass.

15. Apparatus as in claim 7, wherein the angle of rotation of the dihedron is on the order of 70° relative to an original position aligned with the conveyor, and further comprising at least three cameras, the optical axis of a first camera being perpendicular to the direction of the conveyor and the optical axes of a second and a third camera being contained in a horizontal plane, forming an angle of 45° and being disposed symmetrically relative to the first camera.

16. Apparatus as in claim 15, further comprising a fourth camera for imaging an internal part of the carcass, and a lighting device for illuminating the internal part of the carcass.

17. Apparatus as in claim 15, further comprising at least one camera having an optical axis parallel to one of the first, second and third cameras for analyzing the fat coverage of an outer face of the carcass.

18. Apparatus as in claim 7, wherein one surface of the dihedron is inclined at an angle between about 0 to about 20 degrees to the vertical, such that its upper and lower edges are located one on each side of a vertical plane containing the carcass conveyor.

* * * * *